United States Patent
Zarubin

(10) Patent No.: US 10,551,309 B2
(45) Date of Patent: Feb. 4, 2020

(54) METHOD AND SYSTEM TO IMPROVE SCHEME OF OPTICAL NETWORK CABLE AND AUDIO CABLE

(71) Applicant: Comodo Security Solutions, Inc., Clifton, NJ (US)

(72) Inventor: Evgeniy Zarubin, Odessa (UA)

(*) Notice: Subject to any disclaimer, the term of this patent is extended or adjusted under 35 U.S.C. 154(b) by 0 days.

(21) Appl. No.: 15/725,024

(22) Filed: Oct. 4, 2017

(65) Prior Publication Data
US 2018/0188168 A1 Jul. 5, 2018

Related U.S. Application Data

(63) Continuation of application No. 15/216,967, filed on Jul. 22, 2016, now abandoned.

(51) Int. Cl.
*G01N 21/55* (2014.01)
*G01N 21/47* (2006.01)
*G02B 6/42* (2006.01)
*G06K 7/14* (2006.01)

(52) U.S. Cl.
CPC ........ *G01N 21/4785* (2013.01); *G01N 21/55* (2013.01); *G02B 6/4284* (2013.01); *G01N 2201/13* (2013.01); *G06K 7/1417* (2013.01)

(58) Field of Classification Search
CPC .......................... G01N 21/55; G01N 21/4785
USPC ........................................................ 356/432
See application file for complete search history.

(56) References Cited

U.S. PATENT DOCUMENTS

| | | | |
|---|---|---|---|
| 3,809,908 A | 5/1974 | Clanton | |
| 3,963,323 A | 6/1976 | Arnold | |
| 4,169,656 A | 10/1979 | Hodge | |
| 4,678,264 A | 7/1987 | Bowen et al. | |
| 5,064,299 A * | 11/1991 | Hirschmann | G02B 6/4204 385/33 |
| 5,267,337 A | 11/1993 | Kirma | |
| 5,448,661 A * | 9/1995 | Takai | H04B 10/2503 385/17 |
| 5,727,103 A | 3/1998 | Matsusaka et al. | |
| 5,822,478 A | 10/1998 | Kim | |
| 6,179,627 B1 * | 1/2001 | Daly | H01R 13/6658 439/354 |
| 6,974,262 B1 * | 12/2005 | Rickenbach | G02B 6/3817 385/53 |
| 7,942,564 B2 | 5/2011 | Lee et al. | |
| 8,358,893 B1 * | 1/2013 | Sanderson | G02B 6/4415 385/100 |
| 8,452,181 B2 * | 5/2013 | Yasuda | G02B 6/4416 385/101 |
| 8,488,928 B2 * | 7/2013 | Ishimoto | G02B 6/4416 385/101 |

(Continued)

OTHER PUBLICATIONS

S.Iwano, E.Sugita, K.Kanayama, R.Nagase, K.Nakano Design and Performance of Single-mode Plug-in Type Optical-fiber Connectors Journal of Lightwave Technology Nov. 1990, pp. 1750-1759 vol. 8, Issue 11.

(Continued)

*Primary Examiner* — Roy M Punnoose
(74) *Attorney, Agent, or Firm* — Joseph P. Aiena

(57) ABSTRACT

The invention discloses the method of improved optical network cable, where the loss of light is prevented by embedding in it light source and light receiver thus minimizing the consequences of improper joint in optical network.

2 Claims, 6 Drawing Sheets

(56) References Cited

U.S. PATENT DOCUMENTS

| | | | |
|---|---|---|---|
| 8,687,931 B2 | 4/2014 | Sasaoka | |
| 9,304,265 B2 | 4/2016 | Isenhour et al. | |
| 2003/0086664 A1* | 5/2003 | Moisel | G02B 6/4277 385/101 |
| 2005/0117913 A1* | 6/2005 | Hung | G02B 6/4214 398/139 |
| 2006/0088251 A1* | 4/2006 | Wang | G02B 6/4201 385/88 |
| 2007/0237472 A1 | 10/2007 | Aronson et al. | |
| 2007/0258693 A1 | 11/2007 | Becker | |
| 2011/0116751 A1 | 5/2011 | Terlizzi et al. | |
| 2013/0022318 A1 | 1/2013 | Fingler et al. | |
| 2016/0041342 A1 | 2/2016 | Smith et al. | |
| 2016/0334591 A1 | 11/2016 | Wood et al. | |

OTHER PUBLICATIONS

U.S. Patent Office Action dated Apr. 5, 2017 in related U.S. Appl. No. 15/216,967.

U.S. Patent Office Action dated Oct. 31, 2017 in related U.S. Appl. No. 15/216,967.

* cited by examiner

*The First Alternative Embodiment /*

*Audiocable*

METHOD AND SYSTEM TO IMPROVE SCHEME OF OPTICAL NETWORK CABLE AND AUDIO CABLE

CROSS REFERENCE TO RELATED APPLICATIONS

This application is a continuation of and claims the benefit to U.S. Non-Provisional patent application Ser. No. 15/216,967 filed on Jul. 22, 2016.

BACKGROUND

Optical cable is widely used by many companies for installing networks in data centers or Internet exchange points to transmit telephone signals, Internet communication and cable television signals.

There are some evident advantages of fibre optics over other data transmission mediums. For example, fibre optics has rather high bandwidth and it is easy to accommodate increasing bandwidth, using fibre optics. Also fibre has a very low rate of bit error that makes it resistant to electromagnetic interference. Finally fiber provides secure data transmission, since by monitoring an optical network and by carefully measuring its parameters intrusions can be easily detected.

Though while trying to use fibre optics companies' face certain difficulties. Installing optical cable network is still rather costly. Besides there required expensive special test equipment like OTDR (Optical Time Domain Reflectometer) or optical probes, since the similar equipment used for conventional electron-based networking is not applicable to fibre optic network. Another drawback is susceptibility of fibre optics to physical damage during installation or construction activities.

To top it all the structure of optical cable itself has number of disadvantages. In classical scheme buffer tuner and optical diode are located on transmitter, light sensitive detector and buffer amplifier are located on receiver. Cable here is insulated optical fiber with connectors.

So there will be inevitable light (signal) refraction because of different mediums (solid-vaporized-solid). Also there can be decreasing of signal strength (light intensity) because of surface contamination and damaging (scratches). And finally there is a chance for decreasing of light intensity because of non-perfect launch angle of light in optical cable (connector looseness).

Thus, there is a need for alternative approach to fibre optics structure reorganization that would provide still effective data transmission but allow decreasing cost and avoiding possible damage.

SUMMARY OF INVENTION

The new invention idea provides method and system of improved optical network cable, where the loss of light is prevented by embedding in it light source and light receiver thus excluding the consequences of improper joint in optical network.

This invention can be used in any networks in data centers or Internet Exchange Points, providing the higher quality of data transmission between the network nodes. Also this cable is applicable as more effective audio cable.

Such optical cable will provide better connection then usual optical cable. For example, in classical scheme there can be decrease of signal strength because of aging of connectors. But in the proposed by invention scheme influence of external factors (such as surface contamination and damaging, non-perfect connection of the elements—optical diode, optical channel, light sensitive detector—because of aging of the connectors or their bad quality) on the transmission channel is excluded.

This new scheme would allow unifying and simplifying the requirements to standards of output/input signals.

Also using it can save funds since there won't be required expensive equipment for jointing the parts of cable and qualified personnel to work with this equipment.

DETAILED DESCRIPTION

The present invention discloses method and system to prevent loss of light in optical cable by embedding in it light source and light receiver thus excluding the consequences of an improper joint connection in an optical network.

Exemplary embodiments of the present invention are described with reference to the accompanying drawings in detail. Like reference numbers are used throughout the drawings to refer to the same or like parts. Detailed description of well-known functions and structures incorporated herein may be omitted to avoid obscuring the subject matter of the present invention.

The specification and drawings are to be regarded in an illustrative rather than a restrictive sense in order to help understand the present invention. It is apparent to those skilled in the art that various modifications and changes can be made thereto without departing from the broader spirit and scope of the invention.

The invention is not restricted to the details of the foregoing embodiments. The invention extend to any novel one, or any novel combination, of the features disclosed in this specification (including any accompanying claims, abstract and drawings), or to any novel one, or any novel combination, of the steps of any method or process so disclosed.

There are two cases of alternate embodiments of the current scheme of optical network cable.

Figure 1:
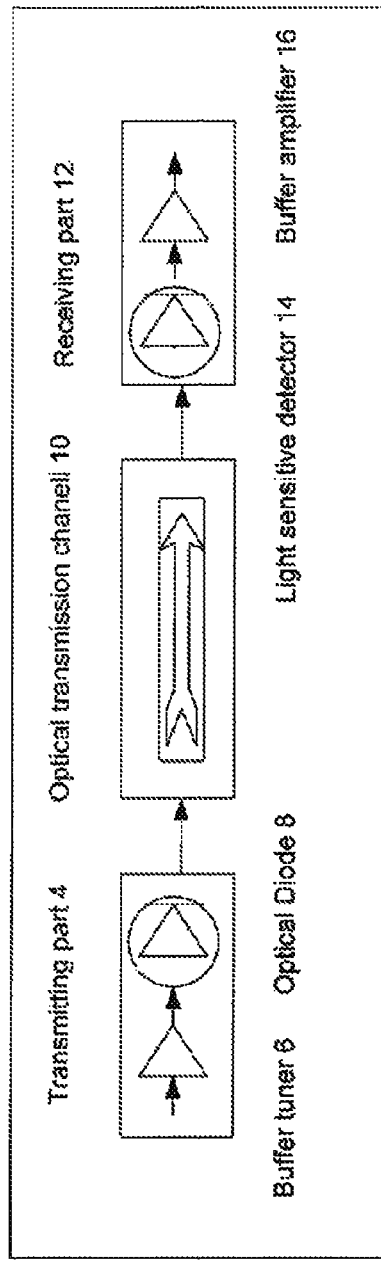
FIG. 1 is a general scheme of optical network cable.

In FIG. 1 the general scheme of optical cable 2 or fibre is shown. The transmitting part 4 comprises buffer tuner 6 and optical diode 8. They are connected in chain through transmission channel 10 with receiving part 12 which combines light sensitive detector 14 and buffer amplifier 16.

The transmission channel 10 here is optical fibre core, which is applicable in installing optical networks and as optical audio cable. Optical fibre can be large in diameter and support multiple light rays or modes concurrently. This type of optical fibre is called multimode fibre. Or fibre core can be made small enough (around 5 microns in diameter) and light modes will be restricted to a single pathway with one length, this fibre will be called single-mode fibre.

Multimode fibre may be used for shorter and/or slower networks while single mode fibre is used for longer networks.

Transmitting part 4 and receiving part 12 may include couplers and wavelength-division multiplexing to transmit bi-directionally over a single fibre as in FTTH PONs passive optical networks or OLANs, optical LANs. Also there can be used wavelength-division multiplexing where it is implemented transmission at several wavelengths of light simultaneously over a single fibre in each direction.

Figure 2A:
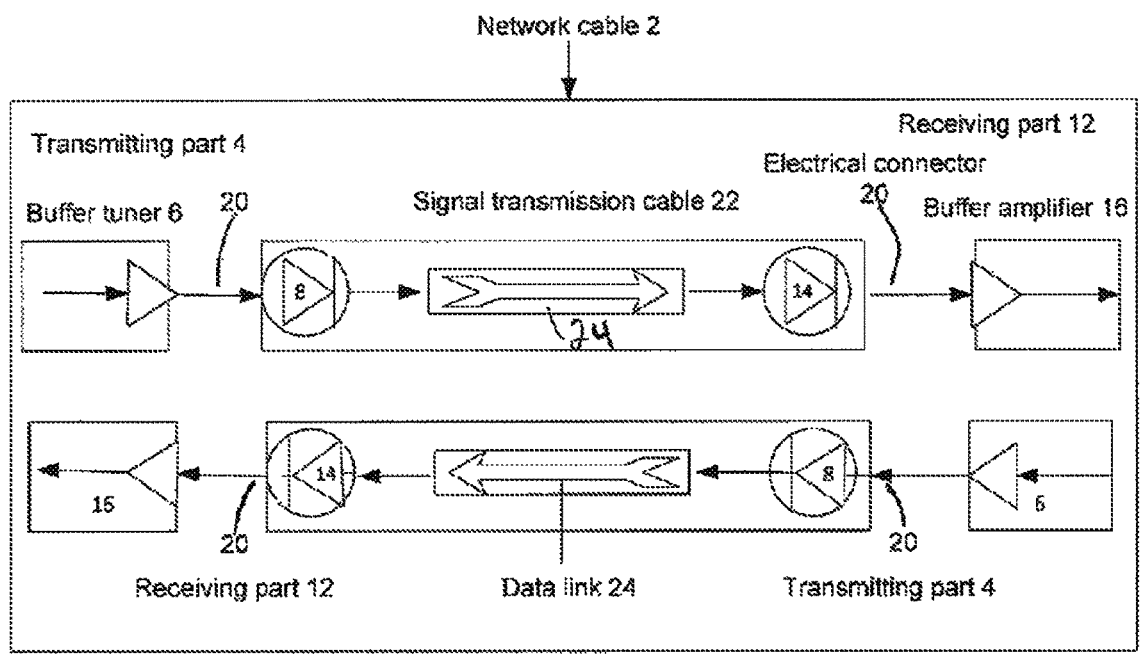
FIG. 2a shows the first possible improvement of scheme of optical network cable.
Figure 2B:
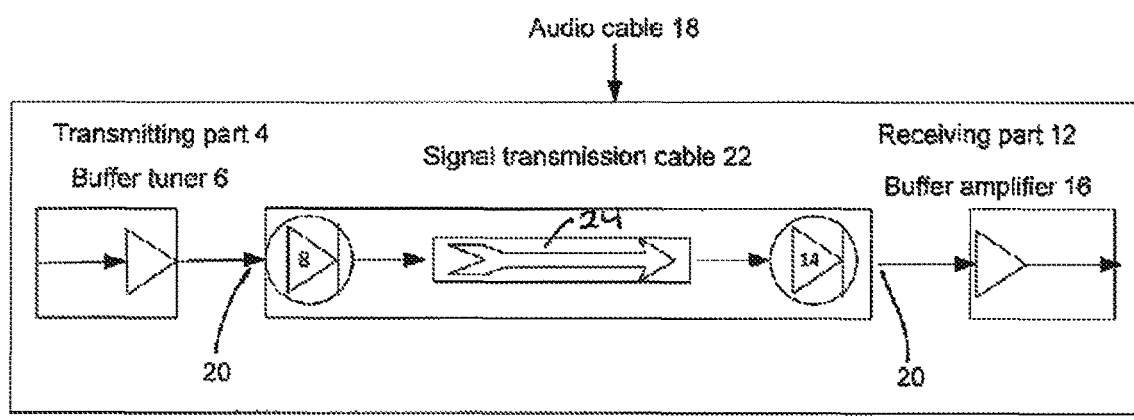
FIG. 2b shows the first possible improvement of scheme of optical audio cable.

FIGS. 2a and 2b demonstrate the first possible improvement of scheme of optical network cable 2 and optical audio cable 18. Here the optical diode 8 of transmitter 4 and light-sensitive detector 14 of receiver 12 are embedded in optical cable 2 and audio cable 18 and thus form the one unit (not sectioned). This scheme grants the higher quality of signal transmission within the characteristics of physical processes in each element of the system. Here the input and output of the optical cable 2 and audio cable 18 is the electrical connector 20 with two pins 23. Electrical connectors 20 joint buffer tuner 6 with signal transmission cable 22 and on the other end of the chain the signal transmission cable 22—with buffer amplifier 16. The probability of the bad connection in electronic circuit is much lower than in optical one.

Figure 3A:
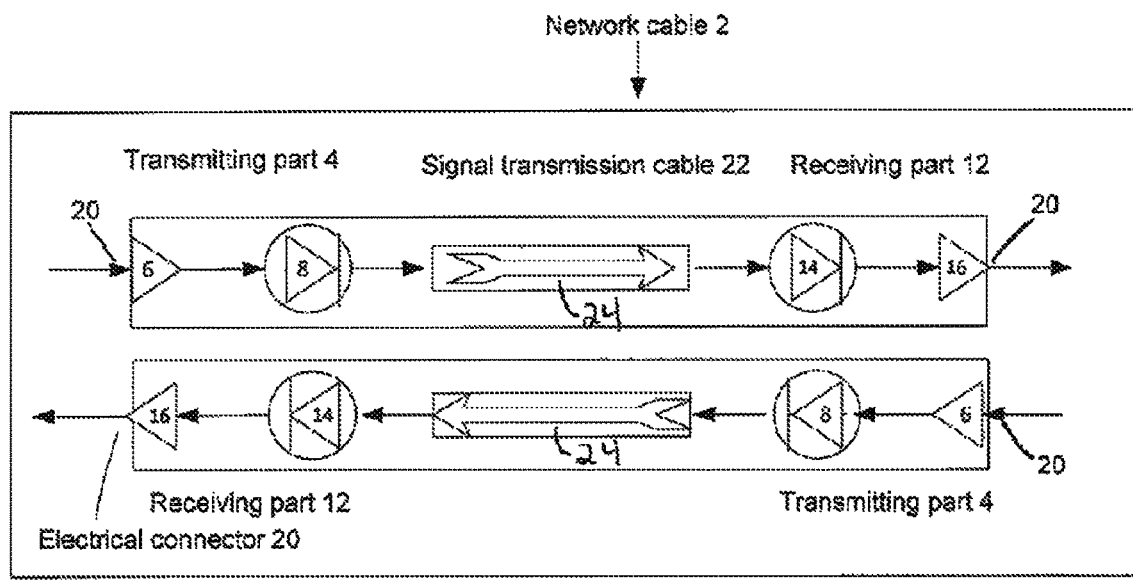
FIG. 3a shows the second possible improvement of scheme of optical network cable.
Figure 3B:
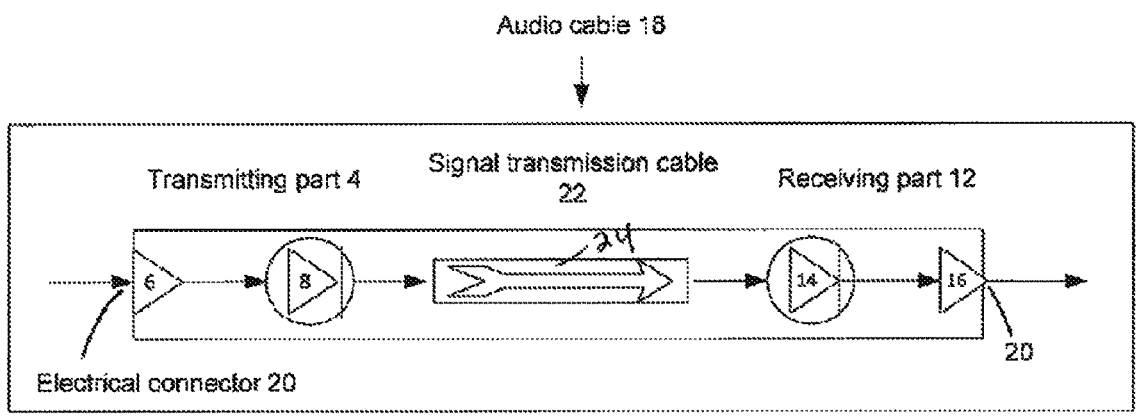
FIG. 3b shows the second possible improvement of scheme of optical audio cable.

FIGS. 3a and 3b demonstrate the second possible improvement of scheme of optical network cable 2 and optical audio cable 18. Here the optical diode 8 and buffer tuner 6 of transmitter 4, and light-sensitive detector 14 and buffer amplifier 16 of receiver 12 are embedded in optical cable 2 and optical audio cable 18 and thus form the one unit (not sectioned). This makes compatibility with other devices even easier. Such approach avoids problems caused by the differences in characteristics of radio elements produced by different companies. Taking into account the modern tendency to minimize the integrated circuit, the physical size of the cable parts, containing the optical elements and tuners, will be small. In this scheme optical cable 2 and optical audio cable 18 have connector 20 with three pins 25: signal line, feed line of tuner, general line.

Figure 4:
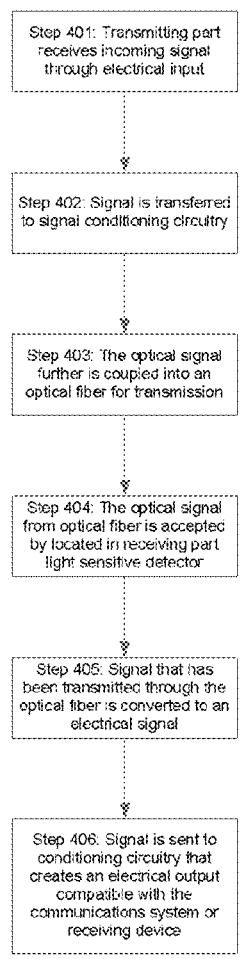
FIG. 4 is a flowchart illustrating a non-limiting exemplary operation of one embodiment of the invention where signal is transmitted over the fibre.

FIG. 4 shows the flowchart of one embodiment of the invention where signal is transmitted over the optical network cable 2 or optical audio cable 18. Individual transmitters and receivers at either end or transceivers that transmit over optical fibres form a fibre optic datalink 24. The typical datalink 24 transmits over two fibres for full duplex links, one fibre in each direction. A datalink 24 includes a transmitting part 4 that converts electrical signals to optical signals, and receiving part 12 that converts optical signals to electrical signals. In step 401 transmitting part 4 receives incoming signal through electrical input. Appropriate interfaces are included in the datalink 24 to mate with the electrical and optical signals it connects with. These are typically standardized electrical and fibre optic connectors 20. In step 402 signals is transferred to signal conditioning circuitry which is driving an optical source, a light-emitting diode or laser that provides the electrical to optical conversion. In step 403 the optical signal further is coupled into an optical fibre for transmission. In case the fibre is not single mode fibre, the special alignment hardware is needed. In step 404 the optical signal from optical fibre is accepted by located in receiving part 12 light sensitive detector 14. In step 405 signals that has been transmitted through the optical fibre is converted to an electrical signal and in step 406 signal is sent to conditioning circuitry that creates an electrical output compatible with the communications system or receiving device. While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated.

What is claimed is:

1. A method to prevent loss of light in optical network cable and audio cable by improving the scheme of optical cable comprising:

converting, by a transmitting part of said optical cable, an incoming electrical signal to an optical signal, said transmitting part having a buffer tuner and an optical diode;

converting, by a receiving part of said optical cable, said optical signal to an outgoing electrical signal, said receiving part having a light sensitive detector and a buffer amplifier;

embedding said optical diode of said transmitting part and said light-sensitive detector of said receiving part in a signal transmission cable of said optical cable thus forming a singular non-sectioned unit to exclude the consequences of an improper joint connection in said optical network cable, said signal transmission cable of said optical cable having a first electrical connector as input and a second electrical connector as output of said signal transmission cable of said optical cable and said audio cable; and jointing through said first electrical connector said buffer tuner with the signal transmission cable at a first end of said signal transmission cable and at a second end of the signal transmission cable jointing said second electrical connector with said buffer amplifier:

transmitting said optical signal over said optical network cable or said optical audio cable via said transmitting part that receives said incoming electrical signal through electrical input;

transferring said incoming electrical signal to signal conditioning circuitry;

coupling said optical signal into an optical fibre for transmission;

accepting said optical signal by said light sensitive detector located in said receiving part;

converting said optical signal that has been transmitted through said optical fibre to said outgoing electrical signal; and sending said electrical signal to conditioning circuitry that creates an electrical output compatible with a communications system or receiving device.

2. A method to prevent loss of light in optical network cable and audio cable by improving the scheme of optical cable comprising:

converting, by a transmitting part of said optical cable, an incoming electrical signal to an optical signal, said transmitting part having a buffer tuner and an optical diode;

converting, by a receiving part of said optical cable, said optical signal to an outgoing electrical signal, said receiving part having a light sensitive detector and a buffer amplifier;

embedding said optical diode and said buffer tuner of said transmitting part and said light-sensitive detector and said buffer amplifier of said receiving part in a signal transmission cable of said optical cable thus forming a singular non-sectioned unit to exclude the consequences of an improper joint connection in said optical network cable, said signal transmission cable of said optical cable having a first electrical connector as input and a second electrical connector as output of said signal transmission cable of said optical cable and said audio cable:

transmitting said optical signal over said optical network cable or said optical audio cable via said transmitting part that receives said incoming electrical signal through electrical input;

transferring said incoming electrical signal to signal conditioning circuitry;

coupling said optical signal into an optical fibre for transmission;

accepting said optical signal by said light sensitive detector located in said receiving part;

converting said optical signal that has been transmitted through said optical fibre to said outgoing electrical signal; and sending said electrical signal to conditioning circuitry that creates an electrical output compatible with a communications system or receiving device.

\* \* \* \* \*